US008187864B2

(12) United States Patent
Wheeler et al.

(10) Patent No.: US 8,187,864 B2
(45) Date of Patent: May 29, 2012

(54) EXCHANGEABLE SHEETS PRE-LOADED WITH REAGENT DEPOTS FOR DIGITAL MICROFLUIDICS

(75) Inventors: Aaron R. Wheeler, Toronto (CA); Irena Barbulovic-Nad, Toronto (CA); Hao Yang, Toronto (CA); Mohamed Abdelgawad, Toronto (CA)

(73) Assignee: The Governing Council of the University of Toronto, Toronto (CA)

( * ) Notice: Subject to any disclaimer, the term of this patent is extended or adjusted under 35 U.S.C. 154(b) by 162 days.

(21) Appl. No.: 12/285,326

(22) Filed: Oct. 1, 2008

(65) Prior Publication Data

US 2010/0081578 A1 Apr. 1, 2010

(51) Int. Cl.
*C12M 1/34* (2006.01)
*C12M 3/00* (2006.01)

(52) U.S. Cl. ................ 435/287.1; 435/287.2; 435/287.9

(58) Field of Classification Search ............... 435/287.1, 435/287.2, 287.9
See application file for complete search history.

(56) References Cited

U.S. PATENT DOCUMENTS

| | | | | |
|---|---|---|---|---|
| 4,569,575 | A | 2/1986 | Le Pesant et al. | |
| 4,636,785 | A | 1/1987 | Le Pesant | |
| 4,818,052 | A | 4/1989 | Le Pesant et al. | |
| 5,486,337 | A | 1/1996 | Ohkawa et al. | |
| 6,352,838 | B1 | 3/2002 | Krulevitch et al. | |
| 6,565,727 | B1 | 5/2003 | Shenderov | |
| 6,726,818 | B2 * | 4/2004 | Cui et al. | 204/403.01 |
| 6,911,132 | B2 | 6/2005 | Pamula et al. | |
| 6,989,234 | B2 | 1/2006 | Kolar et al. | |
| 7,147,763 | B2 | 12/2006 | Elrod et al. | |
| 7,163,612 | B2 | 1/2007 | Sterling et al. | |
| 7,214,302 | B1 | 5/2007 | Reihs et al. | |
| 7,255,780 | B2 | 8/2007 | Shenderov | |
| 7,328,979 | B2 | 2/2008 | Decre et al. | |
| 7,329,545 | B2 | 2/2008 | Pamula et al. | |
| 2002/0043463 | A1 | 4/2002 | Shenderov | |
| 2004/0171169 | A1 | 9/2004 | Kallury et al. | |
| 2004/0211659 | A1 | 10/2004 | Velev | |
| 2005/0115836 | A1 | 6/2005 | Reihs | |
| 2005/0148091 | A1 | 7/2005 | Kitaguchi et al. | |
| 2005/0191759 | A1 | 9/2005 | Pedersen-Bjergaard et al. | |

(Continued)

FOREIGN PATENT DOCUMENTS

WO 2007120241 A2 10/2007

(Continued)

OTHER PUBLICATIONS

Lebrasseur, et al., "Two-dimensional electrostatic actuation of droplets using a single electrode panel and development of disposable plastic film card", Sensors and Actuators A, Apr. 19, 2007, pp. 358-366, vol. 136, No. 1.

(Continued)

*Primary Examiner* — Melanie J Yu

(74) *Attorney, Agent, or Firm* — Lynn C. Schumacher; Hill & Schumacher

(57) ABSTRACT

The present invention provides an exchangeable, reagent pre-loaded sheets which can be temporarily applied to an electrode array on a digital microfluidic device (DMF). The substrate facilitates virtually un-limited re-use of the DMF devices avoiding cross-contamination on the electrode array itself, as well as enabling rapid exchange of pre-loaded reagents while bridging the world-to-chip interface of DMF devices. The present invention allows for the transformation of DMF into a versatile platform for lab-on-a-chip applications.

32 Claims, 5 Drawing Sheets

U.S. PATENT DOCUMENTS

| | | | | |
|---|---|---|---|---|
| 2007/0023929 | A1 | 2/2007 | Kim et al. | |
| 2007/0148763 | A1 | 6/2007 | Huh et al. | |
| 2007/0202538 | A1* | 8/2007 | Glezer et al. | 435/7.1 |
| 2007/0242111 | A1 | 10/2007 | Pamula et al. | |
| 2008/0044914 | A1 | 2/2008 | Pamula et al. | |
| 2008/0156983 | A1 | 7/2008 | Fourrier et al. | |
| 2008/0185339 | A1 | 8/2008 | Delapierre et al. | |
| 2009/0203063 | A1 | 8/2009 | Wheeler et al. | |
| 2010/0311599 | A1 | 12/2010 | Wheeler et al. | |

FOREIGN PATENT DOCUMENTS

| | | | |
|---|---|---|---|
| WO | 2007136386 | A3 | 11/2007 |
| WO | 2008/051310 | | 5/2008 |

OTHER PUBLICATIONS

Hongmei, Yu. "A Plate reader-compatible microchannel array for cell biology assays," The Royal Society of Chemistry 2007, Lab Chip (2007) vol. 7 pp. 288-391.

A.S. Verkman, "Drug Discovery in Academia," Am J Physiol Cell Physiol (2004) vol. 286, pp. 465-474.

Eun Zoo Lee, "Removal of bovine serum albumin using solid-phase extraction with in-situ polymerized stationary phase in a microfluidic device," ScienceDirect, Journal of Chromatography A. (2008) vol. 1187, pp. 11-17.

Hsih Yin Tan, "A lab-on-a-chip for detection of nerve agent sarin in blood," The Royal Society of Chemistry (2008), Lab Chip vol. 8, pp. 885-891.

Mais J. Jebrail. "Digital Microfluidic Method for Protein Extraction by Precipitation," Anal. Chem. (2009) vol. 81, No. 1.

Shih-Kang Fan. "Cross-scale electric manipulations of cells and droplets by frequency-modulated dielectrophoresis and electrowetting" The Royal Society of Chemistry (2008), Lab Chip vol. 8, pp. 1325-1331.

Ting-Hsuan Chen. "Selective Wettability Assisted Nanoliter Sample Generation via Electrowetting-Based Transportation," Proceedings of the Fifth International Conference on Nanochannels, Microchannels and Minichannels (ICNMM) (Jun. 18-20, 2007).

Hyejin Moon. An integrated digital microfluidic chip for multiplexed proteomic sample preparation and analysis by MALDI-MS, The Royal Society of Chemistry (2006), Lab Chip vol. 6, pp. 1213-1219.

Debalina Chatterjee. "Droplet-based microfluidics with nonaqueous solvents and solutions," The Royal Society of Chemistry (2006), Lab Chip vol. 6, pp. 199-206.

Darren R. Link. "Electric Control of Droplets in Microfluidic Devices," Communications, Angew Chem. Int (2006) vol. 45 pp. 2556-2560.

Wheeler Aaron R. "Eletrowetting-Based Microfluidics for Analysis of Peptides and Proteins by Matrix-Assisted Laser Desorption/Ionization Mass Spectrometry," Analytical Chemistry (Aug. 2009) vol. 76, No. 16.

Jamil El-Ali. "Cells on chips," Nature (2006) Insight Review, vol. 442.

Marc A. Unger. "Monolithic Microfabricated Valves and Pumps by Multilayer Soft Lithography," Science (2000) vol. 288.

Adbelgawad et al., "Low-cost rapid-prototyping of digital microfluidics devices", Microfluid Nanofluid (2008) vol. 4 pp. 349-355, Springer-Verlag (2007).

Chuang et al., "Direct Handwriting Manipulation of Droplets by Self-Aligned Mirror-EWOD Across a Dielectric Sheet", Institute of Nanotechnology National Chiao Tung University Hsinchu Taiwan, MEMS (2006) pp. 22-26, Istanbul—Turkey (2006).

* cited by examiner

PRE-LOADED SUBSTRATES FOR DIGITAL MICROFLUIDICS

EXCHANGEABLE SHEETS PRE-LOADED WITH REAGENT DEPOTS FOR DIGITAL MICROFLUIDICS

FIELD OF THE INVENTION

The present invention relates to exchangeable, reagent pre-loaded substrates for digital microfluidics, and more particularly the present invention relates to removable plastic sheets on which reagents are strategically located in pre-selected positions as exchangeable sheets for digital microfluidic devices.

BACKGROUND TO THE INVENTION

Microfluidics deals with precise control and manipulation of fluids that are geometrically constrained to small, typically microliter, volumes. Because of the rapid kinetics and the potential for automation, microfluidics can potentially transform routine bioassays into rapid and reliable tests for use outside of the laboratory. Recently, a new paradigm for miniaturized bioassays has been emerged called "digital" (or droplet based) microfluidics. Digital microfluidics (DMF) relies on manipulating discrete droplet of fluids across a surface of patterned electrodes.[1-10] This technique is analogous to sample processing in test tubes, and is well suited for array-based bioassays in which one can perform various biochemical reactions by merging and mixing those droplets. More importantly, the array based geometry of DMF seems to be a natural fit for large, parallel scaled, multiplexed analyses. In fact, the power of this new technique has been demonstrated in a wide variety of applications including cell-based assays, enzyme assays, protein profiling, and the polymerase chain reaction.

Unfortunately, there are two critical limitations on the scope of applications compatible with DMF—biofouling and interfacing. The former limitation, biofouling, is a pernicious one in all micro-scale analyses—a negative side-effect of high surface area to volume ratios is the increased rate of adsorption of analytes from solution onto solid surfaces. We and others have developed strategies to limit the extent of biofouling in digital microfluidics, but the problem persists as a roadblock, preventing wide adoption of the technique.

The second limitation for DMF (and for all microfluidic systems) is the "world-to-chip" interface—it is notoriously difficult to deliver reagents and samples to such systems without compromising the oft-hyped advantages of rapid analyses and reduced reagent consumption. A solution to this problem for microchannel-based methods is the use of pre-loaded reagents. Such methods typically comprise two steps: (1) reagents are stored in microchannels (or in replaceable cartridges), and (2) at a later time, the reagents are rapidly accessed to carry out the desired assay/experiment. Two strategies have emerged for microchannel systems—in the first, reagents are stored as solutions in droplets isolated from each other by plugs of air[11] or an immiscible fluid[12,13] until use. In a second, reagents are stored in solid phase in channels, and are then reconstituted in solution when the assay is performed.[14-16] Pre-loaded reagents in microfluidic devices is a strategy that will be useful for a wide range of applications. Until now, however, there has been no analogous technique for digital microfluidics.

In response to the twin challenges of non-specific adsorption and world-to-chip interfacing in digital microfluidics, we have developed a new strategy relying on removable polymer coverings.[17-19] After each experiment, a thin film is replaced, but the central infrastructure of the device is reused. This effectively prevents cross-contamination between repeated analyses, and perhaps more importantly, serves as a useful medium for reagent introduction onto DMF devices. To demonstrate this principle, we pre-loaded dried spots of enzymes to the plastic coverings for subsequent use in proteolytic digestion assays. The loaded reagents were found to be active after >1 month of storage in a freezer. As the first technology of its kind, we propose that this innovation may represent an important step forward for digital microfluidics, making it an attractive fluid-handling platform for a wide range of applications.

SUMMARY OF THE INVENTION

The present invention provides removable, disposable plastic sheets which are be pre-loaded with reagents. The new method involves manipulating reagent and sample droplets on DMF devices that have been attached with pre-loaded sheets. When an assay is complete, the sheet can be removed, analyzed, if desired, and the original device can be reused by reattaching a fresh pre-loaded sheet to start another assay.

These removable, disposable plastic films, pre-loaded with reagents, facilitate rapid, batch scale assays using DMF devices with no problems of cross-contamination between assays. In addition, the reagent cartridge devices and method disclosed herein facilitate the use of reagent storage depots. For example, the inventors have fabricated sheets with pre-loaded dried spots containing enzymes commonly used in proteomic assays, such as trypsin or $\alpha$-chymotrypsin. After digestion of the model substrate ubiquitin, the product-containing sheets were evaluated by matrix assisted laser desorption/ionization mass spectrometry (MALDI-MS). The present invention very advantageously elevates DMF to compatibility with diverse applications ranging from laboratory analyses to point-of-care diagnostics.

Thus, an embodiment of the present invention includes a sheet or film pre-loaded with reagents for use with a digital microfluidic device, the digital microfluidic device including an electrode array, said electrode array including an array of discrete electrodes, the digital microfluidic device including an electrode controller, the pre-loaded substrate comprising:

an electrically insulating sheet having a back surface and a front hydrophobic surface, said electrically insulating sheet being removably attachable to said electrode array of the digital microfluidic device with said back surface being adhered to said electrode array, said electrically insulating sheet covering said discrete electrodes for insulating the discrete electrodes from each other and from liquid droplets on the front hydrophobic surface, said electrically insulating sheet having one or more reagent depots located in one or more pre-selected positions on the front hydrophobic surface of the electrically insulating sheet; and wherein in operation the electrode controller being capable of selectively actuating and de-actuating said discrete electrodes for translating liquid droplets over the front hydrophobic surface of the electrically insulating sheet.

In another embodiment of the present invention there is provided a digital microfluidic device, comprising:

a first substrate having mounted on a surface thereof an electrode array, said electrode array including an array of discrete electrodes, the digital microfluidic device including an electrode controller capable of selectively actuating and de-actuating said discrete electrodes;

an electrically insulating sheet having a back surface and a front hydrophobic surface, said electrically insulating sheet being removably attachable to said electrode array of the digital microfluidic device with said back surface being adhered to said array of discrete electrodes, said electrically insulating sheet electrically insulating said discrete electrodes from each other in said electrode array and from liquid droplets on the front hydrophobic surface, said electrically insulating sheet having one or more reagent depots located in one or more pre-selected positions on the front hydrophobic surface of the electrically insulating sheet, said one or more pre-selected positions on said front hydrophobic surface being positioned to be accessible to the liquid droplets actuated over the front hydrophobic surface of the electrically insulating sheet; and wherein liquid droplets are translated across said front hydrophobic surface to said one or more reagent depots by selectively actuating and de-actuating said discrete electrodes under control of said electrode controller.

In an embodiment of the apparatus there may be included a second substrate having a front surface which is optionally a hydrophobic surface, wherein the second substrate is in a spaced relationship to the first substrate thus defining a space between the first and second substrates capable of containing droplets between the front surface of the second substrate and the front hydrophobic surface of the electrically insulating sheet on said electrode array on said the substrate. An embodiment of the device may include an electrode array on the second substrate, covered by a dielectic sheet. In this case the electrode array on the first substrate may be optional and hence may be omitted. There may also be insulating sheets pre-loaded with reagent depots on one or both of the substrates.

The present invention also provides a digital microfluidics method, comprising the steps of;

a) preparing a digital microfluidic device having an electrode array including an array of discrete electrodes, the digital microfluidic device including an electrode controller connected to said array of discrete electrodes for applying a selected pattern of voltages to said discrete electrodes for selectively actuating and de-actuating said discrete electrodes in order to move liquid sample drops across said electrode array in a desired pathway over said discrete electrodes;

b) providing a removably attachable electrically insulating sheet having a back surface and a front working surface, said electrically insulating sheet being removably attached to said electrode array of the digital microfluidic device with said back surface being adhered thereto, said electrically insulating sheet having hydrophobic front surface and one or more reagent depots located in one or more pre-selected positions on the front working surface of the electrically insulating sheet, said one or more pre-selected positions on said front working surface of said electrically insulating sheet are positioned to be accessible to droplets actuated over the front working surface of the electrically insulating sheet;

c) conducting an assay by directing one or more sample droplets over said front working surface to said one or more reagent depots whereby the one or more sample droplets is delivered to said one or more reagent depots which is reconstituted by the one or more sample droplets and mixed with at least one selected reagent contained in the one or more reagent depots;

d) isolating any resulting reaction product formed between said mixed sample droplet and said at least one selected reagent in each of said one or more reagent depots; and e) removing said removably attachable electrically insulating sheet from the surface of the electrode array of the digital microfluidic device and preparing the digital microfluidic device for a new assay.

A further understanding of the functional and advantageous aspects of the invention can be realized by reference to the following detailed description and drawings.

BRIEF DESCRIPTION OF THE DRAWINGS

Embodiments of the present invention are described in greater detail with reference to the accompanying drawings, in which.

DETAILED DESCRIPTION OF THE INVENTION

Generally speaking, the systems described herein are directed to exchangeable, reagent pre-loaded substrates for digital microfluidics devices, particularly suitable for high throughput assay procedures. As required, embodiments of the present invention are disclosed herein. However, the disclosed embodiments are merely exemplary, and it should be understood that the invention may be embodied in many various and alternative forms. The figures are not to scale and some features may be exaggerated or minimized to show details of particular elements while related elements may have been eliminated to prevent obscuring novel aspects.

Therefore, specific structural and functional details disclosed herein are not to be interpreted as limiting but merely as a basis for the claims and as a representative basis for teaching one skilled in the art to variously employ the present invention. For purposes of teaching and not limitation, the illustrated embodiments are directed to exchangeable, reagent pre-loaded substrates for digital microfluidics devices.

As used herein, the term "about", when used in conjunction with ranges of dimensions of particles or other physical or chemical properties or characteristics, is meant to cover slight variations that may exist in the upper and lower limits of the ranges of dimensions so as to not exclude embodiments where on average most of the dimensions are satisfied but where statistically dimensions may exist outside this region. It is not the intention to exclude embodiments such as these from the present invention.

The basic problem to be solved by the present invention is to provide a means of adapting digital microfluidic devices so that they can be used for high throughput batch processing while at the same time avoiding bio-fouling of the DMF devices as discussed above in the Background. To illustrate how problematic bio-fouling is, studies have been carried out by the inventors to ascertain the scope of this problem.

Protein Adsorption on DMF and Cross Contamination Analysis

Figure 1A:
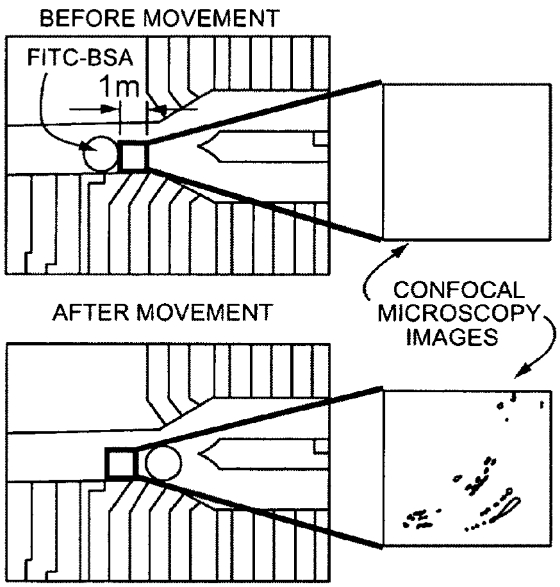
FIG. 1 shows a) protein adsorption from an aqueous droplet onto a DMF device in which the left image shows a device prior to droplet actuation, paired with a corresponding confocal image of a central electrode, the right image shows the same device after a droplet containing FITC-BSA (7 μg/mL) has been cycled over the electrode 4 times, paired with a confocal image collected after droplet movement. The two images were processed identically to illustrate that confocal microscopy can be used to detect the non-specific protein adsorption on device surfaces as a result of digital actuation. The two graphs show cross-contamination on a digital microfluidic device, with (b) showing the mass spectrum of 10 μM angiotensin I (MW 1296); and c) showing the mass spectrum of 1 μM angiotensin II (MW 1046). In the latter case, the droplet was actuated over the same surface as the former on the same device, resulting in cross-contamination.

Confocal microscopy was used to evaluate protein adsorption on surfaces. In general, a droplet containing 7 μg/ml FITC-BSA is translated on a DMF device. Two images were taken on a spot before and after droplet actuation. A residue is left on the surface as a consequence of non-specific protein adsorption during droplet actuation in which it can be detected by confocal microscopy. Such residues can cause two types of problems for DMF: (1) the surface may become sticky, which impedes droplet movement, and (2) if multiple experiments are to be performed, cross-contamination may be a problem. A Fluoview 300 scanning confocal microscope (Olympus, Markam, ON) equipped with an $Ar^+$ (488 nm) laser was used, in conjunction with a 100× objective (N.A. 0.95) for analysis of proteins adsorbed to DMF device surfaces (FIG. 1*a*). Fluorescence from adsorbed labeled proteins was passed through a 510-525 nm band-pass filter, and each digital image was formed from the average of four frames using FluoView image acquisition software (Olympus).

Figure 1B:
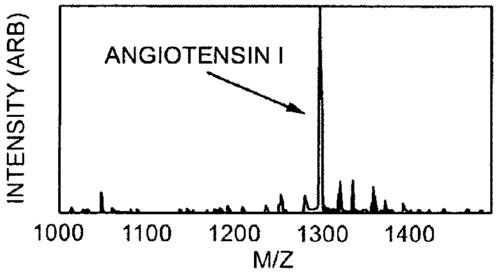
Figure 1C:
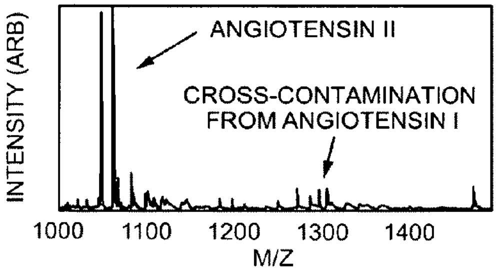

MALDI-MS was used to evaluate the amount of cross contamination of two different peptide samples actuated across the same path on the same device. Specifically, 2 μl droplet of 10 μM angiotensin I in the first run, and 2 μl droplet of 1 μM angiotensin II in the second. As shown in FIG. 1*b*, the spectrum of angiotensin I generated after the first run is relatively clean; however, as shown in FIG. 1*c*, the spectrum of angiotensin II generated is contaminated with residue from the previous run. In these tests, after actuation by DMF, the sample droplets were transferred to a MALDI target for crystallization and analysis, meaning that the cross-contamination comprised both (a) an adsorption step in the first run, and (b) a desorption step in the second run. The intensity from the Angiotensin I contaminant was estimated to be around 10% of most intense Angiotensin II peak (MW 1046). This corresponds to roughly about 1% or 0.1 μM of Angiotensin I fouling non-specifically on the DMF device. Even though the tested peptides are less sticky compare to proteins, this result is in agreement with Luk's reported value, which is less than 8% of FITC-BSA adsorbing to DMF device.[20] In addition to contamination, smooth droplet movement, especially during the run of angiotensin II sample, was obstructed due to non-specific adsorption of previous run. Thus, a higher actuation voltage was required to force the droplet to move over to the next set of electrodes. This however does not always work if the droplet becomes stuck permanently due to high adhesion to the fouled surfaces, increasing actuation voltage will not help in this case, not to mention potential dielectric breakdown and ruin the device if the voltage is too high.

Exchangeable, Pre-Loaded, Disposable Substrates

The present invention provides exchangeable, pre-loaded, disposable substrates on which reagents are strategically located in pre-selected positions on the upper surface. These substrates can be used as exchangeable substrates for use with digital microfluidic devices where the substrate is applied to the electrode array of the digital microfluidics device.

Figure 2:
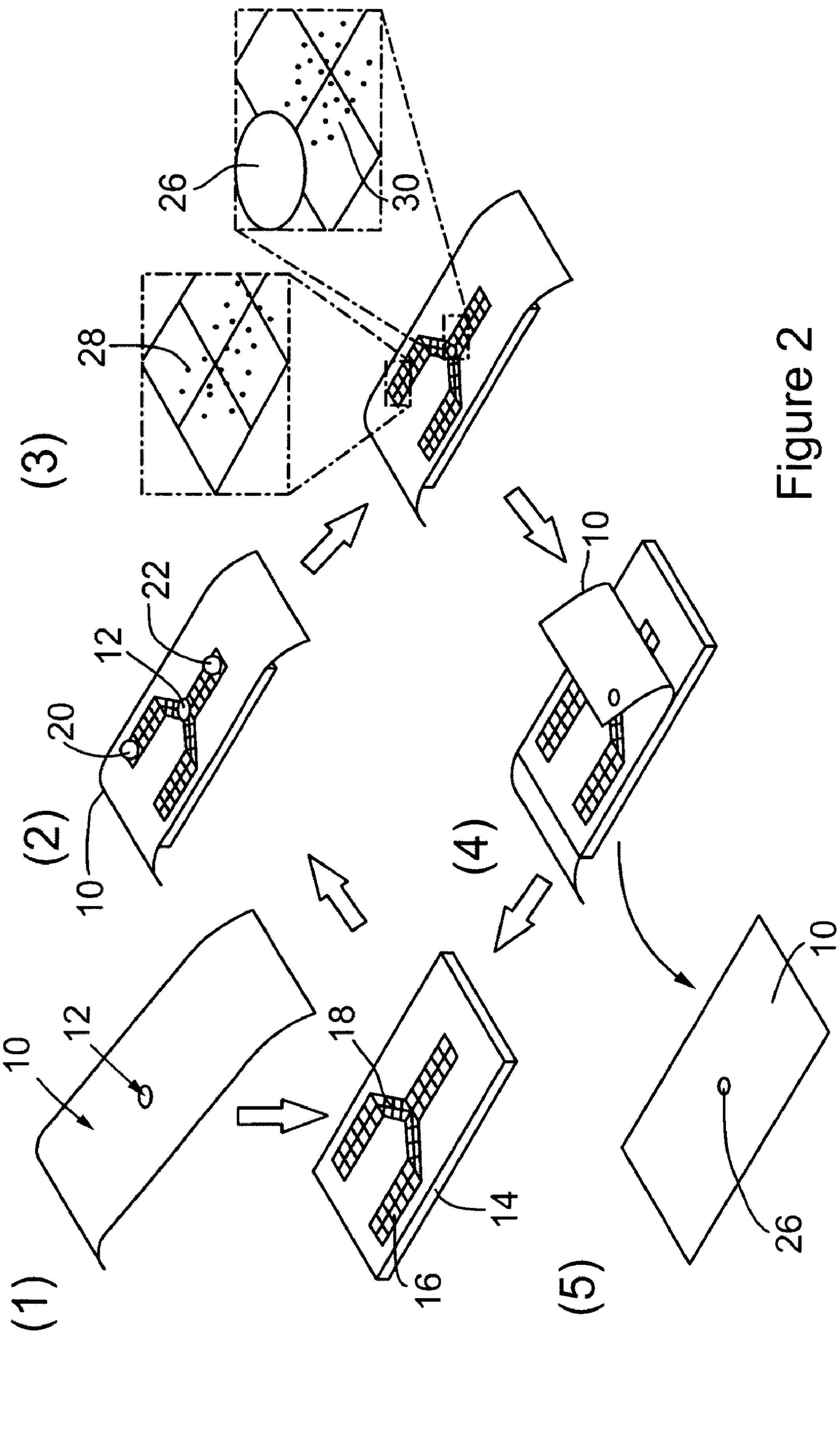
FIG. 2 is a schematic depicting the removable pre-loaded sheet strategy where in step (1) fresh piece of plastic sheet with a dry reagent is affixed to a DMF device; in step (2) reagents in droplets are actuated over on top of the sheet, exposed to the preloaded dry reagent, merged, mixed and incubated to result in a chemical reaction product; in step (3) residue is left behind as a consequence of non-specific adsorption of analytes; and in step (4) the substrate with a product droplet or dried product is peeled off and the product is analyzed if desired.

Referring to FIG. 2, a pre-loaded, electrically insulating disposable sheet shown generally at 10 according to the present invention has one pre-loaded reagent depot 12 mounted on a hydrophobic front surface of electrically insulating sheet 10. This disposable substrate 10 may be any thin dielectric sheet or film so long as it is chemically stable toward the reagents pre-loaded thereon. For example, any polymer based plastic may be used, such as for example saran wrap. In addition to plastic food-wrap, other substrates, including generic/clerical adhesive tapes and stretched sheets of paraffin, were also evaluated for use as replaceable DMF substrates.

The disposable sheet 10 is affixed to the electrode array 16 of the DMF device 14 with a back surface of the sheet 10 adhered to the electrode array 16 in which the reagent depot 12 deposited on the surface of the sheet 10 (across which the reagent droplets are translated) is aligned with pre-selected individual electrode 18 of the electrode array 16 as shown in steps (1) and (2) of FIG. 2. Two reagents droplets 20 and 22 are deposited onto the device prior to an assay. As can be seen from step 3 of FIG. 2, during the assay reagent droplets 20 and 22 are actuated over the top of disposable sheet 10 to facilitate mixing and merging of the assay reagent droplets 20 and 22 with the desired reagent depot 12 over electrode 18.

After the reaction has been completed, the disposable sheet 10 may then be peeled off as shown in step (4) and the resultant reaction products 26 analyzed if desired as shown in step (5). A fresh disposable substrate 10 is then attached to the DMF device 14 for next round of analysis. The product 26 can be also analyzed while the removable substrate is still attached to the device DMF device 14. This process can be recycled by using additional pre-loaded substrates. In addition, the droplets containing reaction product(s) may be split, mixed with additional droplets, incubated for cell culture if they contain cells.

As a consequence, cross contamination is avoided as residues 28 and 30 from assays conducted on a previous disposable sheet 10 will be removed along with the disposable substrate. The assay described above was done using one preloaded reagent 12 but it will be appreciated that the preloaded sheet 10 can be loaded with multiple reagents assayed in series or in parallel with multiple droplet reagents 20 and 22.

In an embodiment of the present invention the pre-loaded electrically insulating sheet 10 and the electrode array may each include alignment marks for aligning the electrically insulating sheet with the electrode array when affixing the electrically insulating sheet to the electrode array such that one or more pre-selected positions on front working surface of the electrically insulating sheet 10 are selected to be in registration with one or more pre-selected discrete actuating electrodes of the electrode array. When the reagent depots are in registration with pre-selected electrodes they may be located over top of a selected electrode or next to it laterally so that it is above a gap between adjacent electrodes.

The disposable substrates may be packaged with a plurality of other substrates and sold with the reagent depots containing one or more reagents selected for specific assay types. Thus the substrates in the package may have an identical number of reagent depots with each depot including an identical reagent composition. The reagent depots preferably include dried reagent but they could also include a viscous gelled reagent.

One potential application of the present invention may be culturing and assaying cells on regent depots. In such applications the reagent depots can include bio-substrate with attachment factors for adherent cells, such as fibronectin, collagen, laminin, polylysine, etc. and any combination thereof. Droplets with cells can be directed to the bio-substrate depots to allow cell attachment thereto in the case of adherent cells. After attachment, cells can be cultured or analyzed in the DMF device.

While the DMF device has been shown in FIG. 2 to have a single substrate with an electrode array formed thereon, it will be appreciated by those skilled in the art that the DMF device may include a second substrate having a front surface which is optionally a hydrophobic surface, wherein the second substrate is in a spaced relationship to the first substrate thus defining a space between the first and second substrates capable of containing droplets between the front surface of the second substrate and the front hydrophobic surface of the electrically insulating sheet on said electrode array on the first substrate. The second substrate may be substantially transparent.

When the front surface of the second substrate is not hydrophobic, the device may include an additional electrically insulating sheet having a back surface and a front hydrophobic surface being removably attachable to the front surface of the second substrate with the back surface adhered to the front surface and additional electrically insulating sheet has one or more reagent depots located in one or more pre-selected positions on the front hydrophobic surface of the electrically insulating sheet.

Additionally there may be included an additional electrode array mounted on the front surface of the second substrate, and including a layer applied onto the additional electrode array having a front hydrophobic surface. The layer applied onto the additional electrode array has a front hydrophobic surface which may be an additional electrically insulating sheet having one or more reagent depots located in one or more pre-selected positions on the front hydrophobic surface.

In this two plate design described above, the first substrate may optionally not have the pre-loaded insulating sheet with reagent depots mounted thereon.

The present invention and its efficacy for high throughput assaying will be illustrated with the following studies and examples, which are meant to be illustrative only and non-limiting.

Experimental Details

Reagents and Materials

Working solutions of all matrixes (α-CHCA, DHB, HPA, and SA) were prepared at 10 mg/mL in 50% analytical grade acetonitrile/deionized (DI) water (v/v) and 0.1% TFA (v/v) and were stored at 4° C. away from light. Stock solutions (10 μM) of angiotensin I, II and bradykinin were prepared in DI water, while stock solutions (100 μM) of ubiquitin and myoglobin were prepared in working buffer (10 mM Tris-HCl, 1 mM $CaCl_2$ 0.0005% w/v Pluronic F68, pH 8). All stock solutions of standards were stored at 4° C. Stock solutions (100 μM) of digestive enzymes (bovine trypsin and α-chymotrypsin) were prepared in working buffer and were stored as aliquots at −80° C. until use. Immediately preceding assays, standards and enzymes were warmed to room temperature and diluted in DI water (peptides) and working buffer (proteins, enzymes, and fluorescent reagents). Fluorescent assay solution (3.3 μM quenched, bodipy-casein and 2 μM rhodamine B in working buffer) was prepared immediately prior to use.

Device Fabrication and Operation

Digital microfluidic devices with 200 nm thick chromium electrodes patterned on glass substrates were fabricated using standard microfabrication techniques. Prior to experiments, devices were fitted with (a) un-modified substrates, or (b) reagent-loaded substrates. When using un-modified substrates (a), a few drops of silicone oil were dispensed onto the electrode array, followed by the plastic covering. The surface was then spin-coated with Teflon-AF (1% w/w in Fluorinert FC-40, 1000 RPM, 60 s) and annealed on a hot plate (75° C., 30 min). When using pre-loaded substrates (b), plastic coverings were modified prior to application to devices. Modification comprised three steps: adhesion of coverings to unpatterned glass substrates, coating with Teflon-AF (as above), and application of reagent depots. The latter step was achieved by pipetting 2 μL droplet(s) of enzyme (6.5 μM trypsin or 10 μM α-chymotrypsin) onto the surface, and allowing it to dry. The pre-loaded sheet was either used immediately, or sealed in a sterilized plastic Petri-dish and stored at −20° C. Prior to use, pre-loaded substrates were allowed to warm to room temperature (if necessary), peeled off of the unpatterned substrate, and applied to a silicone-oil coated electrode array, and annealed on a hot plate (75° C., 2 min). In addition to food wraps, plastic tapes and paraffin have also been used to fit onto the device. Tapes were attached to the device by gentle finger press, whereas paraffin are stretched to about 10 mm thickness and then wrap around the device to make a tight seal free of air bubbles.

Devices had a "Y" shape design of 1 mm×1 mm electrodes with inter-electrode gaps of 10 μm. 2 μL droplets were moved and merged on devices operating in open-plate mode (i.e., with no top cover) by applying driving potentials (400-500 $V_{RMS}$) to sequential pairs of electrodes. The driving potentials were generated by amplifying the output of a function generator operating at 18 kHz, and were applied manually to exposed contact pads. Droplet actuation was monitored and recorded by a CCD camera.

Analysis by MALDI-MS.

Matrix assisted laser desorption/ionization mass spectrometry (MALDI-MS) was used to evaluate samples actuated on DMF devices. Matrix/sample spots were prepared in two modes: conventional and in situ. In conventional mode, samples were manipulated on a device, collected with a pipette and dispensed onto a stainless steel target. A matrix solution was added, and the combined droplet was allowed to dry. In in situ mode, separate droplets containing sample and matrix were moved, merged, and actively mixed by DMF, and then allowed to dry onto the surface. In in situ experiments involving pre-loaded substrates, matrix/crystallization was preceded by an on-chip reaction: droplets containing sample proteins were driven to dried spots containing digestive enzyme (trypsin or α-chymotrypsin). After incubation with the enzyme (room temp., 15 min), a droplet of matrix was driven to the spot to quench the reaction and the combined droplet was allowed to dry. After co-crystallization, substrates were carefully peeled off of the device, and then affixed onto a stainless steel target using double-sided tape. Different matrixes were used for different analytes: a-CHCA for peptide standards and digests, DHB for ultramarker, HPA for oligonucleotides and SA for proteins. At least three replicate spots were evaluated for each sample.

Samples were analyzed using a MALDI-TOF Micro-MX MS (Waters, Milford, Mass.) operating in positive mode. Peptide standards and digests were evaluated in reflectron mode over a mass to charge ratio (m/z) range from 500-2,000. Proteins were evaluated in linear mode over a m/z range from 5,000-30,000. At least one hundred shots were collected per spectrum, with laser power tuned to optimize the signal to noise ratio (S/N). Data were then processed by normalization to the largest analyte peak, baseline subtraction, and smoothed with a 15-point running average. Spectra of enzyme digests were analyzed with the Mascot protein identification package searching the SwissProt database. The database was searched with 1 allowed missed cleavage, a mass accuracy of +/−1.2 Da, and no further modifications.

Peptide/Protein MS Analysis on Exchangeable Substrates

Figure 3:
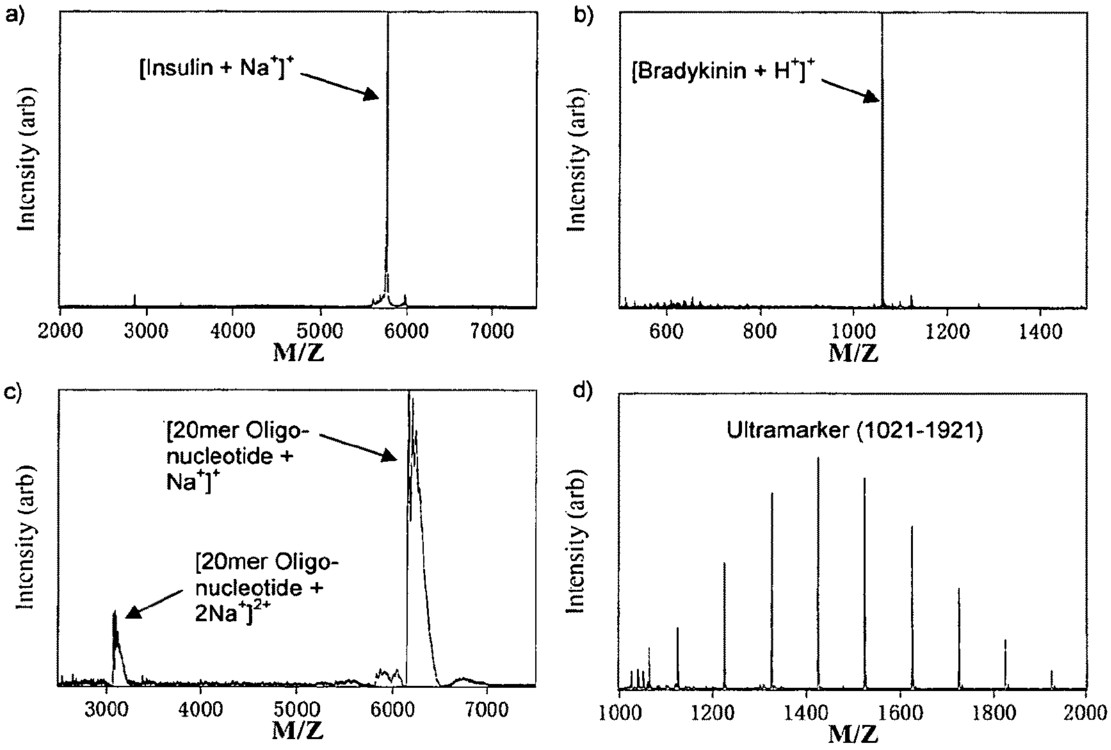
FIG. 3 shows MALDI-MS analysis of different analytes processed on different substrates using a single DMF device a) 35 μM Insulin b) 10 μM Bradykinin c) 10 μM 20 mer DNA Oligonucleotide d) 0.01% ultramarker.

To illustrate the new strategy, four different types of analytes were processed using a single DMF device, using a fresh removable substrate for each run. As shown in FIG. 3, the four analytes included insulin (MW 5733), bradykinin (MW 1060), a 20-mer oligonucleotide (MW 6135), and the synthetic polymer, Ultramark 1621 (MW 900-2200). Each removable substrate was analyzed by MALDI-MS in-situ, and no evidence for cross-contamination was observed. In our lab, conventional devices are typically disposable (used once and then discarded); however, in experiments with removable substrates, we regularly used devices for 9-10 assays with no drop-off in performance. Thus, in addition to eliminating cross-contamination, the removable substrate strategy significantly reduces the fabrication load required to support DMF.

In addition to plastic food-wrap, other substrates, including clerical adhesive tape and stretched sheets of wax film, were also evaluated for use as replaceable substrates. As was the case for food wrap, substrates formed from tape and wax film were found to support droplet movement and facilitate device re-use (data not shown). In addition, substrates formed from these materials were advantageous in that they did not require an annealing step prior to use. Other concerns, however, made these materials less attractive. Coverings formed from adhesive tape tended to damage the actuation electrodes after repeated applications (although presumably, this would not be a problem for low-tack tapes). In addition, as the tape substrates tested were relatively thick (~45 μm), larger driving potentials (~900 $V_{RMS}$) were required for droplet manipulation. In contrast, the thickness of stretched wax was ~10 μm, resulting in driving potentials similar to those used for substrates formed from food wrap. However, the thickness of substrates formed in this manner was observed to be non-uniform, making them less reliable for droplet movement. In summary, it is likely that a variety of different substrates are compatible with the removable covering concept, but because those formed from food-wrap performed best in our hands, we used this material for the experiments reported here.

Two drawbacks to the removable substrate strategy are trapped bubbles and material incompatibility. In initial experiments, bubbles were occasionally observed to become trapped between the substrate and the device surface during application. When a driving potential was applied to an electrode near a trapped bubble, arcing was observed, which damaged the device. We found that this problem could be overcome by moistening the device surface with a few drops of silicone oil prior to application of the plastic film. Upon annealing, the oil evaporates, leaving a bubble-free seal. The latter problem, material incompatibility, is more of a concern. If aggressive solvents are used, materials in the substrate might leach into solution, which could interfere with assays. In our experiments, no contaminant peaks were observed in any MALDI-MS spectra (including in control spectra generated from bare substrate surfaces, not shown), but we cannot rule out the possibility of this being a problem in other settings. Given the apparent wide range of materials that can be used to form substrates (see above), we are confident that alternatives could be used in cases in which Teflon-coated food wrap is not tenable.

Preloaded Substrates and its Stability Analysis.

In exploring exchangeable substrate strategy to overcome fouling and cross-contamination, we realized that the technology could, in addition, serve as the basis for an exciting new innovation for digital microfluidics. By pre-depositing reagents onto substrates (and by having several such substrates available), this strategy transformed DMF techniques into a convenient new platform for rapid introduction of reagents to a device, and can be a solution to the well-known world-to-chip interface problem for microfluidics.[21,22]

Figure 4:
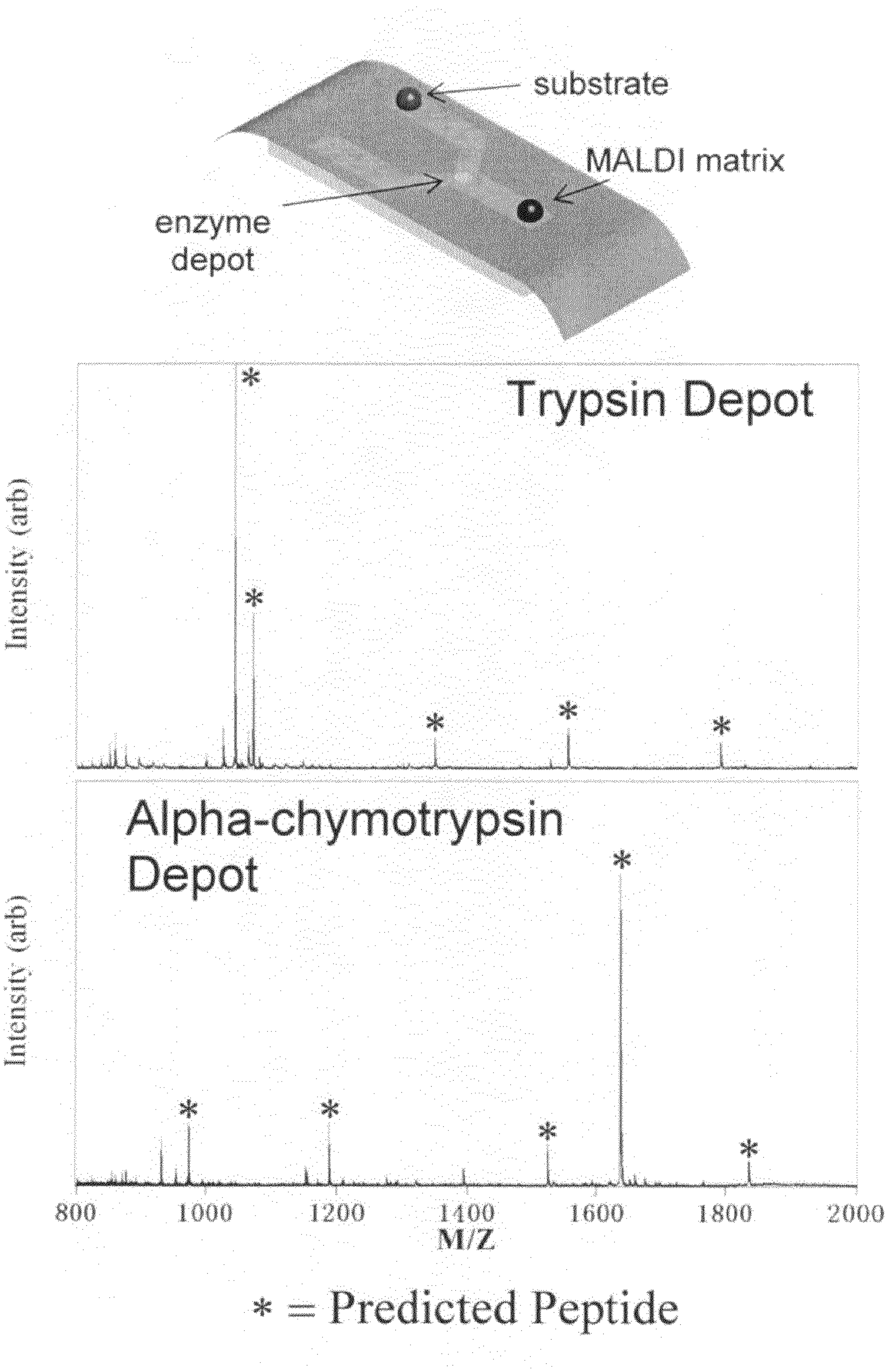
FIG. 4 shows pre-loaded substrate analysis. MALDI peptide mass spectra from pre-spotted (Top) trypsin and (Bottom) α-chymotrypsin digest of ubiquitin were shown, peptide peaks were identified through database search in MASCOT, and the sequence coverage was calculated to be over 50%.

To illustrate the new strategy, we prepared food wraps pre-spotted with dry digestive enzymes, and then used DMF to deliver droplets containing the model substrate, ubiquitin, to the spots. After a suitable incubation period, droplets containing MALDI matrix were delivered to the spot, which was dried and then analyzed. As shown in FIG. 4, MALDI mass spectra were consistent with what is expected of peptide mass fingerprints for the analyte. In fact, when evaluated using the proteomic search engine, MASCOT, the performance was excellent, with sequence identification of 50% or above for all trials.

In optimizing the pre-loaded substrate strategy for protease assays, we observed the method to be quite robust. First, pluronic F68 was used as a solution additive to facilitate movement of the analyte droplet (in this case, ubiquitin); this reagent has been shown to reduce ionization efficiencies for MALDI-MS.[23] Fortunately, the amount used here (0.0005% w/v) was low enough such that this effect was not observed. Second, trypsin and x-chymotrypsin autolysis peaks were only rarely observed, which we attribute to the low enzyme-to-substrate ratio and the short reaction time. Third, in preliminary tests, we determined that the annealing step (75° C., 2 min) did not affect the activity of dried enzymes. In the future, if reagents sensitive to these conditions are used, we plan to evaluate substrates formed from materials that do not require annealing (such as low-tack tape). Regardless, the robust performance of these first assays suggests that the strategy may eventually be useful for a wide range of applications, such as immunoassays or microarray analysis.

As described, the preloaded substrate strategy is similar to the concept of pre-loaded reagents stored in microchannels.[11-16,24] Unlike these previous methods, in which devices are typically disposed of after use, in the present preloaded substrate strategy, the fundamental device architecture can be re-used for any number of assays. Additionally, because the reagents (and the resulting products) are not enclosed in channels, they are in an intrinsically convenient format for analysis. For example, in this work, the format was convenient for MALDI-MS detection, but we speculate that a wide range of detectors could be employed in the future, such as optical readers or acoustic sensors. Finally, although this proof-of-principle work made use of food wrap substrate carrying a single reagent spot, we speculate that in the future, a microarray spotter could be used to fabricate preloaded substrates carrying many different reagents for multiplexed analysis.

To be useful for practical applications, pre-loaded substrates must be able to retain their activity during storage. To evaluate the shelf-life of these reagent spots, we implemented a quantitative protein digest assay. The reporter in this assay, quenched bodipy-labeled casein, has low fluorescence when intact, but becomes highly fluorescent when digested. In this preloaded reagent stability assays, a droplet containing the reporter was driven to a pre-loaded spot of trypsin, and after incubation the fluorescent signal in the droplet was measured in a plate reader (as described previously).[20,25,26] In preliminary experiments with freshly prepared preloaded substrates, it was determined that at the concentrations used, the reaction was complete within 30 minutes. An internal standard (IS), rhodamine B, was used to correct for alignment errors, evaporation effects, and instrument drift over time.

Figure 5:
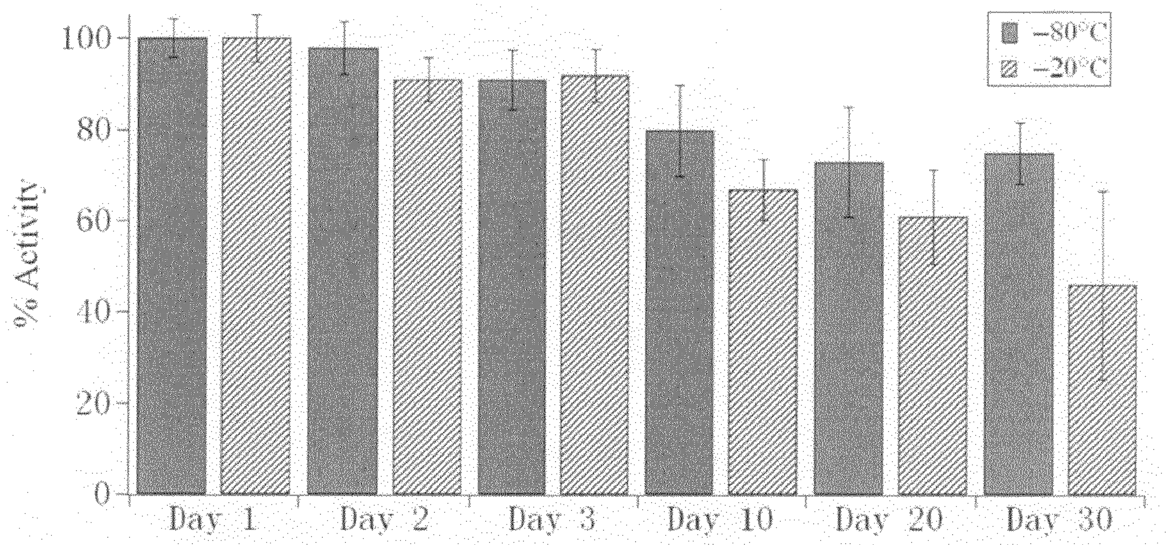
FIG. 5 is a bar graph showing percent activity versus time showing the pre-loaded substrate stability assay in which the fluorescence of protease substrate (BODIPY-casein) and an internal standard were evaluated after storing substrates for 1, 2, 3, 10, 20, and 30 days, the substrates were stored at −20° C. or −80° C. as indicated on the bar graph, and the mean response and standard deviations were calculated for each condition from 5 replicate substrates.

In shelf-life experiments, preloaded substrates were stored for different periods of time (1, 2, 3, 10, 20, or 30 days) at −20° C. or −80° C. In each experiment, after thawing the substrate, positioning it on the device, driving the droplet to the trypsin, and incubating for 30 minutes, the reporter/IS signal ratio was recorded. At least five different substrates were evaluated for each condition. As shown in FIG. 5, shelf-life performance was excellent—substrates stored at −80° C. retained >75% of the original activity for periods as long as 30 days. Substrates stored at −20° C. retained >50% of the original activity over the same period. The difference might simply be the result of different average storage temperature, or might reflect the fact that the −20° C. freezer was used in auto-defrost mode (with regular temperature fluctuations), while the temperature in the −80° C. freezer was constant. Regardless, the performance of these substrates was excellent for a first test, and we anticipate that the shelf-life might be extended in the future by adjusting the enzyme suspension buffer pH or ionic strength or by adding stabilizers such as such as trehalose, a disaccharide that have been used widely in the industry to preserve proteins in the dry state.[27].

In summary, the inventors have developed a new strategy for digital microfluidics, which facilitates virtually un-limited re-use of devices without concern for cross-contamination, as well as enabling rapid exchange of pre-loaded reagents. The present invention allows for the transformation of DMF into a versatile platform for lab-on-a-chip applications.

As used herein, the terms "comprises", "comprising", "including" and "includes" are to be construed as being inclusive and open ended, and not exclusive. Specifically, when used in this specification including claims, the terms "comprises", "comprising", "including" and "includes" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

References (1) Elrod, S. A., Peeters, E. T., Biegelsen, D. K., Dunec, J. L., 2006, U.S. Pat. No. 7,147,763.
(2) Le Pesant, J.-P., 1987, U.S. Pat. No. 4,636,785.
(3) Lee, J., Moon, H., Fowler, J., Schoellhammer, T., Kim, C.-J., "Electrowetting and electrowetting-on-dielectric for microscale liquid handling," *Sensors & Actuators A* 2002, 95, 259-268.
(4) Ohkawa, T., 1996, U.S. Pat. No. 5,486,337.
(5) Pamula, V. K., Pollack, M. G., Paik, P., H., R., Fair, R., 2005, U.S. Pat. No. 6,911,132.
(6) Pollack, M. G., Fair, R. B., Shenderov, A. D., "Electrowetting-based actuation of liquid droplets for microfluidic applications," *Applied Physics Letters* 2000, 77, 1725-1726.
(7) Shenderov, A. D., 2003, U.S. Pat. No. 6,565,727.
(8) Shenderov, A. D., 2007, U.S. Pat. No. 7,255,780.
(9) Washizu, M., "Electrostatic actuation of liquid droplets for microreactor applications," *IEEE Transactions on Industry Applications* 1998, 34, 732-737.
(10) Washizu, M., Kurosawa, O., 1998, Japan 10267801.
(11) Linder, V., Sia, S. K., Whitesides, G. M., "Reagent-loaded cartridges for valveless and automated fluid delivery in microfluidic devices," *Analytical Chemistry* 2005, 77, 64-71.
(12) Hatakeyama, T., Chen, D. L., Ismagilov, R. F., "Microgram-scale testing of reaction conditions in solution using nanoliter plugs in microfluidics with detection by MALDI-MS," *Journal of the American Chemical Society* 2006, 128, 2518-2519.
(13) Zheng, B., Ismagilov, R. F., "A microfluidic approach for screening submicroliter volumes against multiple reagents by using preformed arrays of nanoliter plugs in a three-phase liquid/liquid/gas flow," *Angewandte Chemie—International Edition* 2005, 44, 2520-2523.
(14) Furuberg, L., Mielnik, M., Johansen, I. R., Voitel, J., Gulliksen, A., Solli, L., Karlsen, F., Bayer, T., Schoenfeld, F., Drese, K., Keegan, H., Martin, C., O'Leary, J., Riegger, L., Koltay, P., *The micro active project: Automatic detection of disease-related molecular cell activity, in proceedings of SPIE*-Int. Soc. Opt. Eng. 2007.
(15) Garcia E., Kirkham J. R, Hatch A. V, Hawkins K. R., Yager, P., "Controlled microfluidic reconstitution of functional protein from an anhydrous storage depot.," *Lab on a Chip* 2004, 4, 78-82.
(16) Zimmermann, M., Hunziker, P., Delamarche, E., "Autonomous capillary system for one-step immunoassays," *Biomedical Microdevices* 2008.
(17) Abdelgawad, M., Wheeler, A. R., "Low-cost, rapid-prototyping of digital microfluidics devices," *Microfluidics and Nanofluidics* 2008, 4, 349-355.
(18) Chuang, K. C., Fan, S. K., *Direct handwriting manipulation of droplets by self-aligned mirror-EWOD* across a dielectric sheet, in proceedings of Mems 2006: 19th IEEE International Conference on Micro Electro Mechanical Systems, Technical Digest 2006; 538-541.
(19) Lebrasseur, E., Al-Haq, M. I., Choi, W. K., Hirano, M., Tsuchiya, H., Torii, T., Higuchi, T., Yamazaki, H., Shinohara, E., "Two-dimensional electrostatic actuation of droplets using a single electrode panel and development of disposable plastic film card," *Sensors and Actuators a-Physical* 2007, 136, 358-366.
(20) Luk, V. N., Mo, G. C., Wheeler, A. R., "Pluronic additives: A solution to sticky problems in digital microfluidics," *Langmuir* 2008, 24, 6382-6389.
(21) Fang, Q., Xu, G. M., Fang, Z. L., "A high-throughput continuous sample introduction interface for microfluidic chip-based capillary electrophoresis systems," *Analytical Chemistry* 2002, 74, 1223-1231.
(22) Liu, J., Hansen, C., Quake, S. R., "Solving the "World-to-chip" Interface problem with a microfluidic matrix," *Analytical Chemistry* 2003, 75, 4718-4723.
(23) Boernsen, K. O., Gass, M. A. S., Bruin, G. J. M., Von Adrichem, J. H. M., Biro, M. C., Kresbach, G. M., Ehrat, M., "Influence of solvents and detergents on matrix-assisted laser desorption/ionization mass spectrometry measurements of proteins and oligonucleotides," *Rapid Communications in Mass Spectrometry* 1997, 11, 603-609.
(24) Chen, D. L., Ismagilov, R. F., "Microfluidic cartridges preloaded with nanoliter plugs of reagents: An alternative to 96-well plates for screening," *Current Opinion in Chemical Biology* 2006, 10, 226-231.

(25) Barbulovic-Nad, I., Yang, H., Park, P. S., Wheeler, A. R., "Digital microfluidics for cell-based assays," *Lab on a Chip* 2008, 8, 519-526.

(26) Miller, E. M., Wheeler, A. R., "A digital microfluidic approach to homogeneous enzyme assays," *Analytical Chemistry* 2008, 80, 1614-1619.

(27) Draber, P., Draberova, E., Novakova, M., "Stability of monoclonal igm antibodies freeze-dried in the presence of trehalose," *Journal of Immunological Methods* 1995, 181, 3743.

Therefore what is claimed is:

1. A substrate pre-loaded with reagents for use with a digital microfluidic device, the digital microfluidic device including an electrode array, said electrode array including an array of discrete electrodes, the digital microfluidic device including an electrode controller, the pre-loaded substrate comprising:

an electrically insulating sheet having a back surface and a front hydrophobic surface, said electrically insulating sheet being removably attachable to said electrode array of the digital microfluidic device with said back surface being adhered to said electrode array, said electrically insulating sheet covering said discrete electrodes for insulating the discrete electrodes from each other and from liquid droplets on the front hydrophobic surface, said electrically insulating sheet having one or more reagent depots located in one or more pre-selected positions on the front hydrophobic surface of the electrically insulating sheet;

wherein in operation the electrode controller being capable of selectively actuating and de-actuating said discrete electrodes for translating liquid droplets over the front hydrophobic surface of the electrically insulating sheet;

wherein said one or more pre-selected positions on said front hydrophobic surface of said electrically insulating sheet are positioned to be accessible to droplets translated over said front hydrophobic surface of the electrically insulating sheet under actuation of said discrete electrodes when said insulating sheet is aligned with said electrode array; and wherein said electrically insulating sheet and said electrode array each include alignment marks for aligning the electrically insulating sheet with the said electrode array when affixing the electrically insulating sheet to the electrode array such that said one or more pre-selected positions on said front hydrophobic surface of said electrically insulating sheet are selected to be in registration with one or more pre-selected discrete electrodes of said electrode array.

2. The substrate according to claim 1 wherein said electrically insulating sheet is made of a polymer.

3. The substrate according to claim 1 wherein said electrically insulating sheet is a plastic material.

4. The substrate according to claim 1 wherein said electrically insulating sheet carries a patterned conductive coating that can be used to provide a reference or actuating potential.

5. The substrate according to claim 1 packaged with a plurality of other substrates.

6. The substrate according to claim 5 wherein each of said substrates in said package have an identical number of reagent depots with each depot including an identical reagent composition.

7. The substrate according to claim 1 wherein one or more reagent depots include dried reagent.

8. The substrate according to claim 1 wherein said one or more reagent depots include a viscous gelled reagent.

9. The substrate according to claim 1 wherein each of said one or more reagent depots includes a single reagent.

10. The substrate according to claim 1 wherein said one or more reagent depots are more than one reagent depots, and wherein each reagent depot contains reagent different from reagents in at least one of all other reagent depots.

11. The substrate according to claim 1 wherein each of said one or more reagent depots includes two or more reagents located in each of said one or more reagent depots.

12. The substrate according to claim 1 wherein said electrically insulating sheet includes an adhesive on said back surface thereof which contacts said electrode array for adhering said electrically insulating sheet to said digital microfluidic device.

13. A digital microfluidic device, comprising:

a first substrate having mounted on a surface thereof an electrode array, said electrode array including an array of discrete electrodes, the digital microfluidic device including an electrode controller capable of selectively actuating and de-actuating said discrete electrodes;

an electrically insulating sheet having a back surface and a front hydrophobic surface, said electrically insulating sheet being removably attachable to said electrode array of the digital microfluidic device with said back surface being adhered to said array of discrete electrodes, said electrically insulating sheet electrically insulating said discrete electrodes from each other in said electrode array and from liquid droplets on the front hydrophobic surface, said electrically insulating sheet having one or more reagent depots located in one or more pre-selected positions on the front hydrophobic surface of the electrically insulating sheet, said one or more pre-selected positions on said front hydrophobic surface being positioned to be accessible to the liquid droplets actuated over the front hydrophobic surface of the electrically insulating sheet;

wherein liquid droplets are translated across said front hydrophobic surface to said one or more reagent depots by selectively actuating and de-actuating said discrete electrodes under control of said electrode controller;

wherein said one or more pre-selected positions on said front hydrophobic surface of said electrically insulating sheet are positioned to be accessible to droplets translated over said front hydrophobic surface of the electrically insulating sheet under actuation of said discrete electrodes when said insulating sheet is aligned with said electrode array; and wherein said electrically insulating sheet and said electrode array each include alignment markings for aligning the electrically insulating sheet with the electrode array when affixing the electrically insulating sheet to said electrode array such that said one or more pre-selected positions on said front hydrophobic surface of said electrically insulating sheet are selected to be in registration with one or more pre-selected discrete electrodes of said electrode array.

14. The digital microfluidic device according to claim 13 including a dielectric layer applied directly to said surface of said electrode array sandwiched between said electrode array and said electrically insulating sheet.

15. The digital microfluidic device according to claim 13 wherein said electrically insulating sheet is made of a polymer.

16. The digital microfluidic device according to claim 13 wherein said electrically insulating sheet is a plastic material.

17. The digital microfluidic device according to claim 13 wherein said electrically insulating sheet carries a patterned conductive coating that can be used to provide a reference or actuating potential.

18. The digital microfluidic device according to claim 13 wherein one or more reagent depots include dried reagent.

19. The digital microfluidic device according to claim 13 wherein said one or more reagent depots include a viscous gelled reagent.

20. The digital microfluidic device according to claim 13 wherein each of said one or more reagent depots includes a single reagent.

21. The digital microfluidic device according to claim 13 wherein said one or more reagent depots are more than one reagent depots, and wherein each reagent depot contains reagent different from reagents in at least one of all other reagent depots.

22. The digital microfluidic device according to claim 13 wherein each of said one or more reagent depots includes two or more reagents located in each of said one or more reagent depots.

23. The digital microfluidic device according to claim 13 wherein said electrically insulating sheet includes an adhesive on said back surface thereof which contacts the electrode array for adhering said electrically insulating sheet to said electrode array.

24. The digital microfluidic device according to claim 13 further including a second substrate having a front surface which is optionally a hydrophobic surface, wherein the second substrate is in a spaced relationship to the first substrate thus defining a space between the first and second substrates capable of containing droplets between the front surface of the second substrate and the front hydrophobic surface of the electrically insulating sheet on said electrode array on said first substrate.

25. The digital microfluidic device according to claim 24 wherein the second substrate is substantially transparent.

26. The digital microfluidic device according to claim 24 wherein said front surface of the second substrate is not hydrophobic, including an additional electrically insulating sheet having a back surface and a front hydrophobic surface being removably attachable to said front surface of the second substrate with the back surface adhered to said front surface, said additional electrically insulating sheet having one or more reagent depots located in one or more pre-selected positions on the front hydrophobic surface of the electrically insulating sheet.

27. The digital microfluidic device according to claim 24 including an additional electrode array mounted on the front surface of the second substrate, including a layer applied onto the additional electrode array having a front hydrophobic surface.

28. The digital microfluidic device according to claim 27 wherein said layer applied onto the additional electrode array having a front hydrophobic surface is an additional electrically insulating sheet having one or more additional reagent depots located in one or more pre-selected positions on the front hydrophobic surface of said additional electrically insulating sheet.

29. A substrate pre-loaded with reagents for use with a digital microfluidic device, the digital microfluidic device including an electrode array, said electrode array including an array of discrete electrodes, the digital microfluidic device including an electrode controller, the pre-loaded substrate comprising:

an electrically insulating sheet having a back surface and a front hydrophobic surface, said electrically insulating sheet being removably attachable to said electrode array of the digital microfluidic device with said back surface being adhered to said electrode array, said electrically insulating sheet covering said discrete electrodes for insulating the discrete electrodes from each other and from liquid droplets on the front hydrophobic surface, said electrically insulating sheet having one or more reagent depots located in one or more pre-selected positions on the front hydrophobic surface of the electrically insulating sheet;

wherein in operation the electrode controller being capable of selectively actuating and de-actuating said discrete electrodes for translating liquid droplets over the front hydrophobic surface of the electrically insulating sheet;

wherein said one or more pre-selected positions on said front hydrophobic surface of said electrically insulating sheet are positioned to be accessible to droplets translated over said front hydrophobic surface of the electrically insulating sheet under actuation of said discrete electrodes when said insulating sheet is aligned with said electrode array; and wherein said electrically insulating sheet carries a patterned conductive coating that can be used to provide a reference or actuating potential.

30. The substrate according to claim 29 wherein said electrically insulating sheet and said electrode array each include alignment marks for aligning the electrically insulating sheet with the said electrode array when affixing the electrically insulating sheet to the electrode array such that said one or more pre-selected positions on said front hydrophobic surface of said electrically insulating sheet are selected to be in registration with one or more pre-selected discrete electrodes of said electrode array.

31. A digital microfluidic device, comprising:

a first substrate having mounted on a surface thereof an electrode array, said electrode array including an array of discrete electrodes, the digital microfluidic device including an electrode controller capable of selectively actuating and de-actuating said discrete electrodes;

an electrically insulating sheet having a back surface and a front hydrophobic surface, said electrically insulating sheet being removably attachable to said electrode array of the digital microfluidic device with said back surface being adhered to said array of discrete electrodes, said electrically insulating sheet electrically insulating said discrete electrodes from each other in said electrode array and from liquid droplets on the front hydrophobic surface, said electrically insulating sheet having one or more reagent depots located in one or more pre-selected positions on the front hydrophobic surface of the electrically insulating sheet, said one or more pre-selected positions on said front hydrophobic surface being positioned to be accessible to the liquid droplets actuated over the front hydrophobic surface of the electrically insulating sheet;

wherein liquid droplets are translated across said front hydrophobic surface to said one or more reagent depots by selectively actuating and de-actuating said discrete electrodes under control of said electrode controller; and wherein said one or more pre-selected positions on said front hydrophobic surface of said electrically insulating sheet are positioned to be accessible to droplets translated over said front hydrophobic surface of the electrically insulating sheet under actuation of said discrete electrodes when said insulating sheet is aligned with said electrode array; and wherein said electrically insulating sheet carries a patterned conductive coating that can be used to provide a reference or actuating potential.

32. The digital microfluidic device according to claim 31 wherein said electrically insulating sheet and said electrode array each include alignment markings for aligning the electrically insulating sheet with the electrode array when affixing the electrically insulating sheet to said electrode array such that said one or more pre-selected positions on said front hydrophobic surface of said electrically insulating sheet are selected to be in registration with one or more pre-selected discrete electrodes of said electrode array.

* * * * *